(12) United States Patent
Ishihama et al.

(10) Patent No.: US 6,545,755 B1
(45) Date of Patent: Apr. 8, 2003

(54) MICRO-RAMAN SPECTROSCOPY SYSTEM FOR IDENTIFYING FOREIGN MATERIAL ON A SEMICONDUCTOR WAFER

(75) Inventors: Masaru Ishihama, Saitama (JP); Hiroyuki Hattori, Tokyo (JP); Shuichi Muraishi, Tokyo (JP); Katsuhide Ueda, Tokyo (JP)

(73) Assignees: Jeol Ltd., Tokyo (JP); Jeol Liosonic Co. Ltd., Tokyo (JP)

( * ) Notice: Subject to any disclaimer, the term of this patent is extended or adjusted under 35 U.S.C. 154(b) by 141 days.

(21) Appl. No.: 09/723,318

(22) Filed: Nov. 27, 2000

(30) Foreign Application Priority Data

Nov. 26, 1999 (JP) .............................. 11-336335
Oct. 26, 2000 (JP) ...................... 2000-326572

(51) Int. Cl.[7] .................................................. G01J 3/44
(52) U.S. Cl. .................................. 356/301; 356/237.3
(58) Field of Search ................................. 356/301, 303, 356/433, 73, 318, 237.2–237.5; 250/458.1, 459.1, 461.1, 559.41

(56) References Cited

U.S. PATENT DOCUMENTS 5,377,004 A    12/1994  Owen et al. ................ 356/301
5,841,139 A *  11/1998  Sostek et al. ............. 356/237.2
6,067,154 A *   5/2000  Hossain et al. .......... 356/237.3
6,069,690 A *   5/2000  Xu et al. ................ 250/339.05
6,288,782 B1 *  9/2001  Worster et al. ............. 356/394

\* cited by examiner

*Primary Examiner*—F. L. Evans
*Assistant Examiner*—Kara Geisel
(74) *Attorney, Agent, or Firm*—Webb Ziesenheim Logsdon Orkin & Hanson, P.C.

(57) ABSTRACT

A micro-Raman spectroscopy system capable of making effective use of the unique analyzing capabilities of Raman spectroscopy and still capable of employing information about foreign materials obtained by a separate foreign material inspection system. The micro-Raman spectroscopy system uses a sample stage having a function of reproducing an image of a foreign material on a wafer under an optical microscope, based on positional information previously obtained from foreign materials by the separate foreign material inspection system. Furthermore, the micro-Raman spectroscopy system has a function of searching a built-in database for the substance of the foreign material on the wafer, using a Raman spectrum presently obtained from the foreign material. The system includes a Raman analysis optical system and a Raman spectrometer that are connected by optical fiber.

16 Claims, 2 Drawing Sheets

MICRO-RAMAN SPECTROSCOPY SYSTEM FOR IDENTIFYING FOREIGN MATERIAL ON A SEMICONDUCTOR WAFER

BACKGROUND OF THE INVENTION

1. Field of the Invention

The present invention relates to a micro-Raman spectroscopy system used for non-destructive analysis of foreign materials adhering to surfaces of semiconductor wafers.

2. Description of the Related Art

Semiconductor devices, such as VLSI and ULSI devices, have been fabricated with decreasing dimensions and higher scales of device integration, and a new generation of technology is introduced every three or four years. With this trend, the fabrication yield tends to deteriorate. Accordingly, there is a demand for improvement of the fabrication yield to reduce the fabrication cost.

It is said that low yields in fabrication of VLSI and ULSI devices are caused by microscopic foreign materials which adhere to surfaces of semiconductor wafers during fabrication and hinder correct printing of patterns of integrated circuits. Therefore, in order to improve the yield, it is important to identify the foreign materials and to prevent their adhesion.

A micro-Raman spectroscopy system that is a combination of an optical microscope and a laser Raman spectrometer has enjoyed wide acceptance as a means for identifying the components of microscopic samples. In particular, laser light is introduced to the microscope. The light is focused on a microscopic sample placed under the microscope. Scattering light from the microscopic sample is gathered by the microscope and introduced to the Raman spectrometer. In this way, Raman spectra are obtained.

Scattering light from the sample includes elastic scattering light and inelastic scattering light. Generally, elastic scattering light is known as Rayleigh scattering light, while inelastic scattering light is known as Raman scattering light. Since Raman scattering light is about six orders of magnitude weaker (i.e., 1/1,000,000) than Rayleigh scattering light, the Rayleigh scattering light must be removed by an optical filter and spectrally resolved to obtain a Raman spectrum. The chemical components of the sample can be identified by analyzing the Raman spectrum.

An available means for observing the morphologies of foreign materials on a semiconductor wafer is to use an optical review microscope system having so-called review capability. Specifically, the coordinate values of a foreign material have been already measured. The coordinates are reproduced under a microscope, and an observation of the foreign material is made. A sample stage on which a sample is placed is controlled by a computer. The coordinate values of the foreign material are entered into the computer. The sample stage is moved into a desired position to bring the foreign material immediately under the optical microscope. In this way, the morphologies of the foreign material can be observed.

Also, a method using a review SEM (scanning electron microscope) instead of an optical microscope has been invented. This enables observation of finer morphologies of foreign materials. This system is generally known as a review SEM system.

The prior art micro-Raman spectroscopy system of the construction described above has the problem that it has no review capability. Therefore, it is quite difficult to bring a foreign material on a wafer into the measuring position under a microscope. Silicon wafers are now taken as an example. Wafers generally have diameters of as large as 8 inches (200 mm). It is very difficult to search for micrometer-to-submicrometer foreign materials on such wafers only with a microscope. In the field of semiconductor fabrication, therefore, there are dedicated foreign material inspection systems for searching for foreign materials and displaying their coordinate positions and sizes. However, a conventional micro-Raman spectroscopy system having no review capability cannot make use of results of inspections of foreign materials (e.g., positional information) obtained by a dedicated foreign material inspection system. As a result, the features of Raman spectroscopy having excellent component-analyzing capabilities cannot be utilized for inspections of foreign materials on semiconductor wafers.

On the other hand, where the coordinates of the positions of foreign materials obtained by a dedicated foreign material inspection system and information about their sizes should be utilized, the user must rely on an optical review microscope system or on a review SEM system. In particular, information about foreign materials on a wafer is recorded by a foreign material inspection system. The wafer is placed on a sample stage according to the information about the foreign materials. Each foreign object is moved into the field of view of the optical review microscope or review SEM and observed as a microscope image. The name of the substance of the foreign material is estimated from the results of observation of the morphology. However, limitations are imposed on this method of estimating the substance name only with observation of the morphology. Therefore, in review SEM, for example, an energy dispersive X-ray spectrometer (EDS) is used in combination. Atomic names are judged from the characteristic X-rays arising from the foreign material. Relying on EDS is more effective than relying on only observation of morphologies. However, it is still impossible to judge organic materials and light elements.

SUMMARY OF THE INVENTION

In view of the foregoing, it is an object of the present invention to provide a micro-Raman spectroscopy system which is capable of making effective use of the unique analyzing capabilities of Raman spectroscopy and still capable of employing information about foreign materials obtained by a separate foreign material inspection system.

This object is achieved in accordance with the teachings of the present invention by a micro-Raman spectroscopy system for observing morphologies of a foreign material on a wafer, the micro-Raman spectroscopy system having an optical microscope for observing the morphologies of the foreign material on the wafer, a sample stage having a function of moving the foreign material into the field of view of the optical microscope, a wafer transport mechanism for taking the wafer from a wafer cassette and setting the wafer on the sample stage, at least one Raman-exciting laser for exciting chemical bonds in the foreign material on the wafer, at least one Raman analysis optical system, a Raman spectrometer, and a control means for controlling the sample stage, the wafer transport mechanism, and the Raman spectrometer. The Raman analysis optical system brings the optical axis of the Raman-exciting laser into coincidence with the optical axis of the optical microscope to direct laser light to the foreign material on the wafer. The Raman analysis optical system also acts to take Raman scattering light out of the optical axis of the optical microscope, the Raman scattering light being emitted from the foreign material excited with the laser light. The Raman spectrometer spectroscopically analyzes the Raman scattering light taken from the foreign material on the wafer by the Raman analysis optical system. This micro-Raman spectroscopy system is characterized in that the control means drives the sample stage according to positional information about the foreign material previously obtained by a separate foreign material inspection system, the sample stage having the wafer set thereon. Thus, an image of the foreign material is reproduced within the field of view of the optical microscope.

In one feature of this embodiment of the present invention, the optical microscope described above is equipped with a CCD camera.

In another feature of this embodiment, the optical path between the Raman-exciting laser and the foreign material on the wafer includes at least one of a reflecting mirror and optical lenses.

In a further feature of this embodiment, the optical path between the Raman analysis optical system and the Raman spectrometer is composed of at least optical fiber.

In a still other feature of this embodiment, the control means described above is a computer.

In a yet other feature of this embodiment, the micro-Raman spectroscopy system has a function of searching a built-in database for at least the name of a substance forming the foreign material, using a Raman spectrum presently obtained from the foreign material.

The present invention also provides a micro-Raman spectroscopy system having an optical microscope for observing morphologies of a foreign material on a wafer, a sample stage having a function of moving the foreign material into the field of view of the optical microscope, a wafer transport mechanism for taking the wafer from a wafer cassette and setting the wafer on the sample stage, at least one Raman-exciting laser for exciting chemical bonds in the foreign material on the wafer, at least one second (non-Raman) exciting laser for exciting the foreign material on the wafer, a selector means for passing only one of laser light from the Raman-exciting laser and laser light from the second exciting laser, at least two spectroscopic analysis optical systems, a Raman spectrometer, a non-Raman spectrometer, and a control means for controlling the sample stage, the wafer transport mechanism, the Raman spectrometer, and the non-Raman spectrometer. The spectroscopic analysis optical systems bring the optical axes of the exciting lasers including the Raman-exiting laser into coincidence with the optical axis of the optical microscope and directs laser light to the foreign material on the wafer. The spectroscopic optical systems also act to take excited light out of the optical axis of the optical microscope, the excited light arising from the foreign material excited with the laser light. The Raman spectrometer spectroscopically analyzes the excited light taken from the foreign material on the wafer by the Raman analysis optical system. The non-Raman spectrometer spectroscopically analyzes excited light taken from the foreign material on the wafer by the spectroscopic optical system other than the Raman analysis optical system. This micro-Raman spectroscopy system is characterized in that the control means drives the sample stage according to positional information on the foreign material previously obtained by a separate foreign material inspection system, the sample stage having the wafer set thereon. Thus, an image of the foreign material is reproduced within the field of view of the optical microscope.

In one feature of this embodiment, the optical microscope described above is equipped with a CCD camera.

In another feature of this embodiment, the optical path between the Raman-exciting laser and the foreign material on the wafer includes at least one of a reflecting mirror and optical lenses.

In a further feature of this embodiment, the second (non-Raman) exciting laser includes at least one of a photoluminescence-exciting laser and a fluorescence-exciting laser.

In yet another feature of this embodiment, the selector means for switching the laser light is a movable mirror.

In still another feature of this embodiment, the optical path between the Raman analysis optical system and the Raman spectrometer is composed of at least optical fiber.

In an additional feature of this embodiment, the optical path between the spectroscopic optical system other than the Raman analysis optical system and the non-Raman spectrometer is composed of at least optical fiber.

In a yet additional feature of this embodiment, the spectroscopic analysis optical system other than the Raman analysis optical system includes at least one of a photoluminescence-exciting laser and a fluorescence-exciting laser.

In a yet further feature of this embodiment, the second, non-Raman spectrometer includes at least one of a photoluminescence spectrometer and a fluorescence spectrometer.

In another feature of this embodiment, the control means is a computer.

In another feature of this embodiment, the micro-Raman spectroscopy system has a function of searching a built-in database for at least the names of substances forming the foreign material using various spectra of the foreign material.

Other objects and features of the invention will appear in the course of the description thereof, which follows.

DESCRIPTION OF THE PREFERRED EMBODIMENTS

Figure 1:
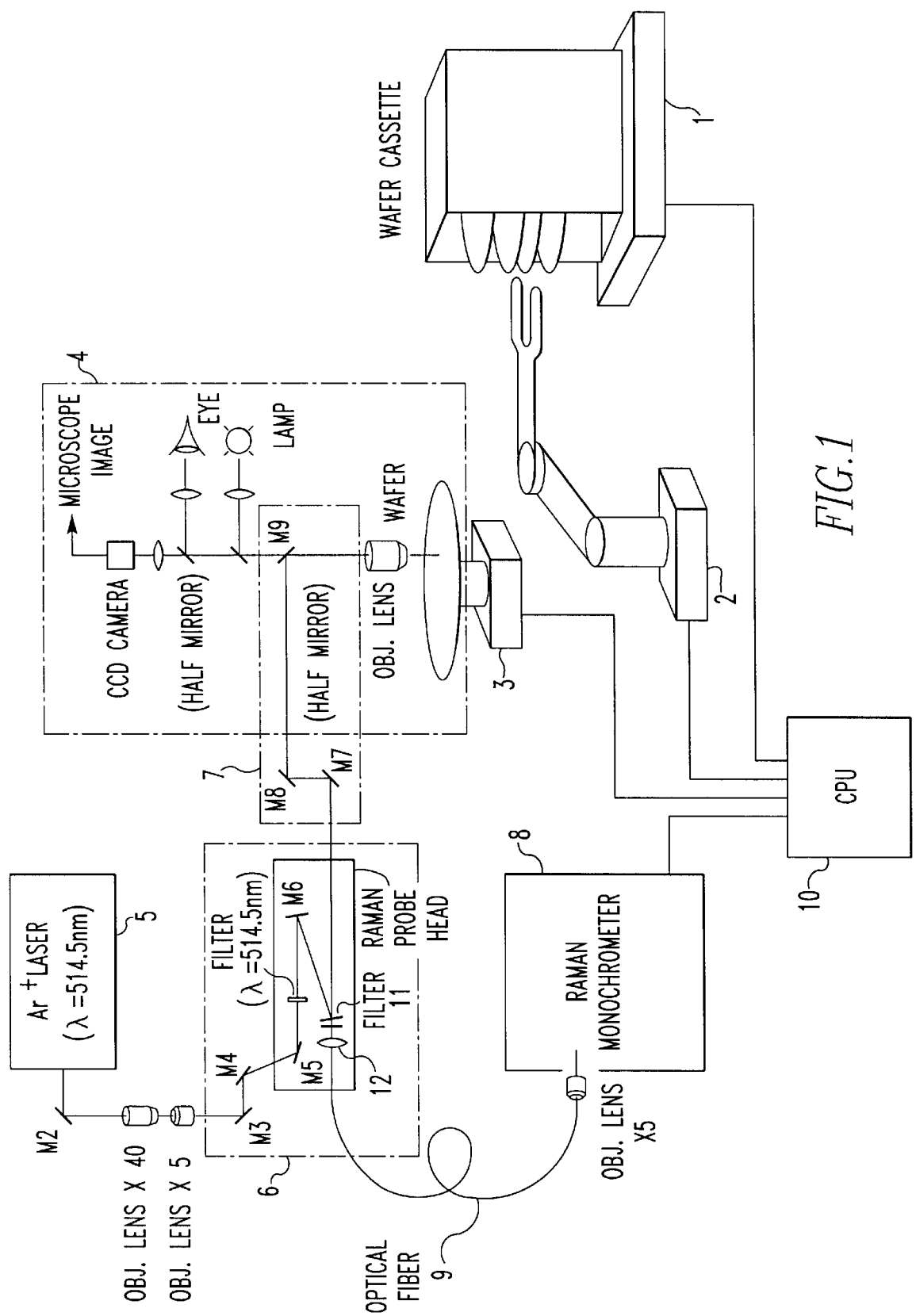
FIG. 1 is a block diagram of a micro-Raman spectroscopy system in accordance with one embodiment of the present invention.

The preferred embodiments of the present invention are hereinafter described by referring to the accompanying drawings. Referring to FIG. 1, there is shown a micro-Raman spectroscopy system in accordance with the present invention. This system has a wafer cassette stage 1 carrying a wafer cassette thereon. The wafer cassette holds wafers therein. The wafers in the wafer cassette carried on the wafer cassette stage are transported to a sample stage 3 under an optical microscope 4 by a wafer transport mechanism 2. The coordinates of the position of a foreign material on each wafer have been previously detected and recorded by a separate foreign material inspection system. The sample stage 3 responds to commands to move the foreign material into the field of view of the microscope according to the previously recorded coordinates. The foreign material is automatically transported to immediately under the microscope.

Returning scattering light from the optical microscope 4 described above is guided to a Raman spectrometer 8 by a connecting optical system 6. The optical axis of the optical microscope 4, the optical axis of laser light emanating from a Raman-exciting laser 5, and the optical axis of the connecting optical system 6 are brought into coincidence by a laser introduction optical system 7. The returning scattering light from the optical microscope 4 is guided to the Raman spectrometer 8 by optical fiber 9 through the laser introduction optical system 7 and the connecting optical system 6. The wafer cassette stage 1, the wafer transport mechanism 2, the sample stage 3, and the Raman spectrometer 8 are all controlled by a computer 10.

The connecting optical system 6 has a portion acting as an optical filter 11 that filters out Rayleigh scattering light from the scattering light emitted from the sample to thereby transmit only Raman scattering light, as well as a portion acting as an optical lens 12 for focusing the Raman scattering light transmitted through the optical filter 11 onto the optical fiber 9. These may also be collectively referred to as the Raman analysis optical system.

One feature of this optical system is that the Raman optical system connecting the Raman-exciting laser 5 and the foreign material on the wafer is composed of the reflecting mirror and the optical lenses without using optical fiber. The laser light can be directly directed to the foreign material on the wafer. Hence, the laser light can be focused up to its diffraction limit before hitting the foreign material. The positional resolution of Raman phenomenon can be enhanced to the level of the diffraction limit of the laser light.

Another feature of this optical system is that optical fiber is used on the incident side of the Raman spectrometer 8, i.e., on the side that receives Raman scattering light. This permits the optical path to be bent at will and increases the number of degrees of freedom in installing the Raman spectrometer 8. Therefore, the Raman spectrometer 8 can be mounted under the microscope 4, thus making the system more compact. Alternatively, the Raman spectrometer 8 may be mounted remotely from the microscope 4.

The micro-Raman spectroscopy system constructed in this way in accordance with the present embodiment operates in the manner now described. First, the wafer transport mechanism 2 takes one wafer from the wafer cassette on the wafer cassette stage 1 and places it on the sample stage 3 under instructions from the computer 10. The positions of foreign materials on wafers have been already measured by a separate foreign material inspection system, and information about these positions was sent to the computer 10, where the information is stored. The computer 10 drives the sample stage 3 according to the information about the position of an object of foreign material on the wafer placed in position, thus placing the wafer in such a way that an image of the foreign material is placed within the field of view of the optical microscope 4.

Illuminating light from the light source of the optical microscope 4 is directed to the foreign material on the wafer. The user can observe the morphologies of the foreign material with the naked eye or with a CCD camera. Laser light emitted from the Raman-exciting laser 5 (e.g., an Argon laser) is directed to the foreign material along the optical axis of the optical microscope 4 via the connecting optical system 6 and via the laser introduction optical system 7, thus exciting chemical bonds in the substance forming the foreign material. Scattering light produced from the excited foreign material is taken out of the optical axis of the optical microscope 4 via the laser introduction optical system 7 and via the connecting optical system 6. Rayleigh scattering light is filtered out by the optical filter 11. Then, only the Raman scattering light is focused by the optical lens 12 and introduced into the optical fiber 9.

The Raman scattering light introduced into the optical fiber is spectrally resolved by the Raman spectrometer 8 and sent as a Raman spectrum to the computer 10. Raman spectra derived from various substances have been previously prepared and stored as a database in the computer 10. The computer 10 searches the database for a Raman spectrum in agreement with the presently obtained spectrum. Thus, at least the substance of the foreign material is identified. That is, the name of the substance can be found. In this way, the chemical component of the foreign material observed under the optical microscope can be identified in a short time. The user can know the origin of the foreign material.

It is to be noted that the present embodiment is not limited to the above embodiment. For example, a photoluminescence-exciting laser, a fluorescence-exciting laser, or other exciting laser may be prepared in addition to the Raman-exciting laser 5. The system may be designed to perform photoluminescence or fluorescence spectroscopy as well as Raman spectroscopy by switching the used exciting laser between these two exciting lasers.

Figure 2:
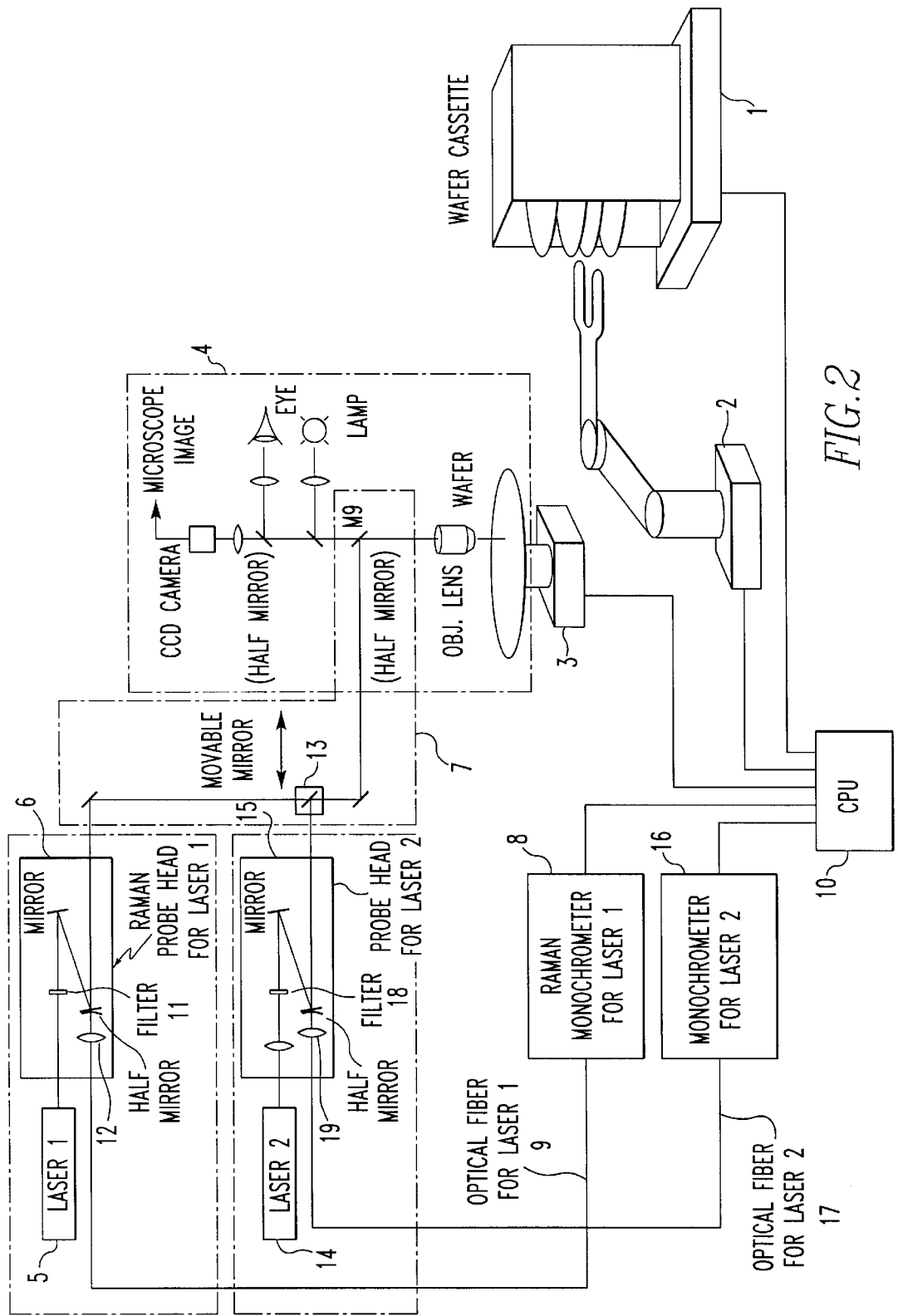
FIG. 2 is a block diagram of a micro-Raman spectroscopy system in accordance with another embodiment of the present invention.

Referring to FIG. 2, there is shown a micro-Raman spectroscopy system in accordance with another embodiment of the present invention. This system has a wafer cassette stage 1 carrying a wafer cassette thereon. The wafer cassette holds wafers therein. Each wafer in the wafer cassette carried on the wafer cassette stage 1 is transported to a sample stage 3 under an optical microscope 4 by a wafer transport mechanism 2. The coordinates of the position of a foreign material on each wafer have been previously detected and recorded by a separate foreign material inspection system. The sample stage 3 has a moving function of moving the foreign material into the field of view of the microscope according to the previously recorded coordinates. The foreign material is automatically transported to immediately under the microscope.

Returning scattering light from the optical microscope 4 described is above is guided to a Raman spectrometer 8 by a connecting optical system 6. The optical axis of the optical microscope 4, the optical axis of laser light emanating from a Raman-exciting laser 5, and the optical axis of the connecting optical system 6 are brought into coincidence by a laser introduction optical system 7. The returning scattering light from the optical microscope 4 is guided to the Raman spectrometer 8 by optical fiber 9 through the laser introduction optical system 7 and the connecting optical system 6.

The laser introduction optical system 7 has a movable mirror 13. A second exciting laser 14, such as a photoluminescence-exciting laser or a fluorescence-exciting laser, is mounted alongside the Raman-exciting laser 5. The used laser light is switched between the laser light from the Raman-exciting laser 5 and the laser light from the second exciting laser 14 by the movable mirror 13. The selected laser light is guided onto the sample on the sample stage 3 via the connecting optical system 15. The optical axis of the optical microscope 4, the optical axis of the laser light from the second exciting laser 14, and the optical axis of the connecting optical system 15 for guiding the returning exciting light from the optical microscope 4 to a second spectrometer 16, such as a photoluminescence spectrometer or fluorescence spectrometer, are brought into coincidence by the laser introduction optical system 7. Therefore, the returning exciting light from the optical microscope 4 is guided to the second spectrometer 16 by optical fiber 17 through the laser introduction optical system 7 and the connecting optical system 15.

The wafer cassette stage 1, the wafer transport mechanism 2, the sample stage 3, the Raman spectrometer 8, and the second spectrometer 16, such as a photoluminescence or fluorescence spectrometer, are all controlled by a computer 10. The connecting optical systems 6 and 15 have portions acting as optical filters 11 and 18, respectively, that filter out Rayleigh scattering light from the scattering light arising from the sample, as well as portions acting as optical lenses 12 and 19, respectively, for focusing the exciting light transmitted through the optical filters onto the optical fiber.

One feature of this optical system is that the optics connecting the Raman-exciting laser 5 and the second exciting laser 14 with the foreign material on the wafer are composed of the reflecting mirror and the optical lenses without using optical fiber. The laser light can be directly directed to the foreign material on the wafer. Hence, the laser beam can be focused up to its diffraction limit before hitting the foreign material. The resolution at the observational position can be enhanced to the level of the diffraction limit of the laser light.

Another feature of this optical system is that optical fiber is used on the incident side of the Raman spectrometer 8 and on the incident side of the second spectrometer 16, such as a photoluminescence or fluorescence spectrometer, i.e., on the side that receives the exciting light. This permits the optical path to be bent at will and increases the number of degrees of freedom in installing the Raman spectrometer 8 and the second spectrometer 16, such as a photoluminescence or fluorescence spectrometer. Therefore, the Raman spectrometer 8 and the second spectrometer 16 can be mounted under the microscope 4, thus making the system more compact. Alternatively, the Raman spectrometer 8 and the second spectrometer 16 may be mounted remotely from the microscope 4.

The micro-Raman spectroscopy system constructed in this way in accordance with the present embodiment operates in the manner described now. When Raman spectroscopy should be performed, the wafer transport mechanism 2 takes one wafer from the wafer cassette on the wafer cassette stage 1 and places it on the sample stage 3 under instructions from the computer 10. The positions of foreign materials on wafers have been already measured by a separate foreign material inspection system, and information about these positions was sent to the computer 10, where the information is stored. The computer 10 drives the sample stage 3 according to the information about the position of a foreign material on the wafer placed in position, thus moving the wafer in such a way that an image of the foreign material is placed within the field of view of the optical microscope 4.

Illuminating light from the light source of the optical microscope 4 is directed to the foreign material on the wafer. The user can observe the morphologies of the foreign material with the naked eye or with a CCD camera. Laser light emitted from the Raman-exciting laser 5 (e.g., an Argon laser) is directed to the foreign material along the optical axis of the optical microscope 4 via the connecting optical system 6 and via the laser introduction optical system 7, thus exciting chemical bonds in a substance forming the foreign material. Obviously, it is necessary at this time to move the movable mirror 13 in the laser introduction optical system 7 off the optical axis connecting the Raman-exciting laser 5 and the optical microscope 4.

Scattering light produced from the excited foreign material is taken out from the optical axis of the optical microscope 4 via the laser introduction optical system 7 and via the connecting optical system 6. Rayleigh scattering light is filtered out by the optical filter 11. Then, only the Raman scattering light is focused by the optical lens 12 and introduced into the optical fiber 9.

The Raman scattering light introduced into the optical fiber 9 is spectrally resolved by the Raman spectrometer 8 and sent as a Raman spectrum to the computer 10. Raman spectra derived from various substances have been previously prepared and stored as a database in the computer 10. The computer 10 searches the database for a Raman spectrum in agreement with the presently obtained spectrum. Thus, at least the substance of the foreign material is identified. That is, the name of the substance can be found. In this way, the chemical component of the foreign material observed under the optical microscope can be identified in a short time. The user can know the origin of the foreign material.

If the user wants to perform an analysis in exactly the same sample position by photoluminescence spectroscopy or fluorescence spectroscopy as in Raman spectroscopy, the movable mirror 13 in the laser introduction optical system 7 is moved to the optical axis connecting the Raman-exciting laser 5 and the optical microscope 4, thus blocking this optical axis. Laser light from the second exciting laser 14 is directed along the optical axis of the optical microscope 4 to the foreign material via the connecting optical system 15 and via the laser introduction optical system 7.

Photoluminescent or fluorescent light emitted from the excited foreign material is taken out of the optical axis of the optical microscope 4 via the laser introduction optical system 7 and the connecting optical system 15. After Rayleigh scattering light is removed by the optical filter 18, only the photoluminescent or fluorescent light is focused by the optical lens 19 and introduced to the optical fiber 17.

The photoluminescent or fluorescent light introduced into the optical fiber 17 is spectrally resolved by the second spectrometer 16, such as a photoluminescence or fluorescence spectrometer, and sent as a photoluminescence or fluorescence spectrum to the computer 10. Photoluminescence or fluorescence spectra derived from various substances have been previously prepared and stored as a database in the computer 10. The computer 10 searches the database for a photoluminescence or fluorescence spectrum coincident with a presently obtained spectrum. Thus, at least the substance of the foreign material is identified. That is, the name of the substance can be found. In this way, the chemical component of the foreign material observed under the optical microscope can be identified in a short time. The user can know the origin of the foreign material.

In the present embodiment, one Raman-exciting laser and one non-Raman exciting laser are juxtaposed. Each kind of exciting laser is not limited to one laser unit. Each kind of exciting laser can consist of two or more laser units. Furthermore, the present invention is also applicable to a micro-Raman spectroscopy system that has plural Raman-exciting lasers alone and is not equipped with any non-Raman exciting laser.

Moreover, in the present embodiment, when laser light is directed to a sample to excite photoluminescence, a connecting optical system consisting of a reflecting mirror and optical lenses is used. Many of exciting lasers used for photoluminescence analyses are large-sized lasers, such as UV lasers. In addition, photoluminescence analyses are used not only for analyses of foreign materials but also for local analyses of samples. Therefore, the used laser beam needs to be less sharply focused than in cases of Raman spectroscopy and fluorescence spectroscopy. Accordingly, as long as photoluminescence is excited, optical fiber may be used in the connecting optical system for the laser light to give flexibility to the locations in which the exciting lasers are mounted.

As described in detail thus far, the micro-Raman spectroscopy system in accordance with the present invention uses an optical microscope having review capability and so it is possible to automatically search a wafer surface for a foreign material and perform Raman spectroscopy. Since a Raman spectrum database has been built, the name of a substance can be quickly found by searching the database using the obtained Raman spectrum. Furthermore, exciting laser light is focused by a reflecting mirror and optical lenses and directed to a foreign material, and scattering light from the foreign material is guided to a Raman spectrometer via optical fiber. Consequently, the laser light can be focused to its diffraction limit during irradiation. Also, the location at which the Raman spectrometer is mounted can be set at will. Additionally, the laser introduction optical system is fitted with a movable mirror to use plural optical axes interchangeably. Therefore, analyses can be made in exactly the same sample location by Raman spectroscopy and photoluminescence or fluorescence spectroscopy.

Having thus described our invention with the detail and particularity required by the Patent Laws, what is desired protected by Letters Patent is set forth in the following claims.

What is claimed is:

1. A micro-Raman spectroscopy system comprising:
    an optical microscope for observing a field of view on a wafer for observation of morphologies of a foreign material on the wafer;
    a sample stage having a function of moving the foreign material into the field of view of the optical microscope;
    a wafer transport mechanism for taking the wafer from a wafer cassette and setting the wafer on the sample stage;
    at least one Raman-exciting laser for exciting chemical bonds in the foreign material on the wafer;
    an optical path not including an optical fiber formed between said Raman-exciting laser and the foreign material on the wafer includes at least one of a reflecting mirror and optical lenses;
    at least one Raman analysis optical system for bringing the optical axis of the Raman-exciting laser into coincidence with the optical axis of the optical microscope to direct laser light to the foreign material on the wafer, said Raman analysis optical system also acting to take Raman scattering light emitted from the foreign material excited by the laser light out of the optical axis of the optical microscope;
    an optical path formed between said Raman spectroscopy optical system and said Raman spectrometer is composed of at least optical fiber;
    a Raman spectrometer for spectroscopically analyzing the Raman scattering light taken from the foreign material on the wafer by the Raman analysis optical system; and
    a control means for controlling the sample stage, the wafer transport mechanism, and the Raman spectrometer, said control means acting to drive the sample stage according to positional information on the foreign material previously obtained by a separate foreign material inspection system, the sample stage having the wafer set thereon, to reproduce an image of the foreign material within the field of view of the optical microscope.

2. The micro-Raman spectroscopy system of claim 1, wherein said optical microscope is equipped with a CCD camera.

3. The micro-Raman spectroscopy system of claim 1, wherein said control means is a computer.

4. The micro-Raman spectroscopy system of claim 1, further comprising a searching function of searching a built-in database for at least the name of a substance forming the foreign material using a Raman spectrum obtained from the foreign material by a present measurement.

5. A micro-Raman spectroscopy system comprising:
    an optical microscope having a field of view and used for observation of morphologies of a foreign material on a wafer;
    a sample stage having a function of moving the foreign material on the wafer into the field of view of the optical microscope;
    a wafer transport mechanism for taking the wafer from a wafer cassette and setting the wafer on the sample stage;
    at least one Raman-exciting laser for exciting chemical bonds in the foreign material on the wafer;
    at least one second exciting laser not associated with Raman spectroscopy;
    a selector means for selecting one from laser light from the Raman-exciting laser and laser light from the second exciting laser;
    at least two spectroscopic optical systems for bringing the optical axes of the exciting lasers including the Raman-exiting laser into coincidence with the optical axis of the optical microscope and directing laser light to the foreign material on the wafer, said at least two spectroscopic optical systems including a Raman analysis optical system, said at least two spectroscopic optical systems acting to take excited light off the optical axis of the optical microscope, the excited light arising from the foreign material excited with the laser light;
    a Raman spectrometer for spectroscopically analyzing the excited light taken from the foreign material on the wafer by the Raman analysis optical system;
    a second spectrometer different from a Raman spectrometer, said second spectrometer acting to spectroscopically analyze excited light taken from the foreign material on the wafer by the spectroscopic optical system other than the Raman analysis optical system; and
    a control means for controlling the sample stage, the wafer transport mechanism, the Raman spectrometer, and the second spectrometer, said controlling means acting to drive the sample stage according to positional information on the foreign material previously obtained by a separate foreign material inspection system, the sample stage having the wafer set thereon, to reproduce an image of the foreign material within the field of view of the optical microscope.

6. The micro-Raman spectroscopy system of claim 5, wherein said optical microscope is equipped with a CCD camera.

7. The micro-Raman spectroscopy system of claim 5, wherein an optical path formed between said Raman-exciting laser and the foreign material on the wafer includes at least one of a reflecting mirror and optical lenses.

8. The micro-Raman spectroscopy system of claim 5, wherein an optical path formed between said second exciting laser and the foreign material on the wafer includes at least one of a reflecting mirror and optical lenses.

9. The micro-Raman spectroscopy system of claim 5 or 8, wherein said second exciting laser includes at least one of a photoluminescence-exciting laser and a fluorescence-exciting laser.

10. The micro-Raman spectroscopy system of claim 5, wherein said selector means for selecting one laser light is a movable mirror.

11. The micro-Raman spectroscopy system of claim 5, wherein an optical path formed between the Raman analysis optical system and the Raman spectrometer is composed of at least optical fiber.

12. The micro-Raman spectroscopy system of claim 5, wherein an optical path formed between the spectroscopic optical system other than the Raman analysis optical system and said second spectrometer is composed of at least optical fiber.

13. The micro-Raman spectroscopy system of claim 5 or 12, wherein said spectroscopic analysis optical system other than said Raman analysis optical system includes at least one of a photoluminescence-exciting laser and a fluorescence-exciting laser.

14. The micro-Raman spectroscopy system of claim 5 or 12, wherein said second spectrometer other than a Raman spectrometer includes at least one of a photoluminescence spectrometer and a fluorescence spectrometer.

15. The micro-Raman spectroscopy system of claim 5, wherein said control means is a computer.

16. The micro-Raman spectroscopy system of claim 5, further including a function of searching a built-in database for at least the names of the substances of the foreign material using various spectra obtained from the foreign material.

* * * * *